United States Patent
Huang et al.

(10) Patent No.: US 9,605,800 B2
(45) Date of Patent: Mar. 28, 2017

(54) MEDICAL CEILING PENDANT, AND APPARATUS AND METHOD FOR OVERALL PACKING MEDICAL CEILING PENDANT

(71) Applicant: MAQUET (SUZHOU) CO., LTD., Suzhou (CN)

(72) Inventors: Jiasheng Huang, Suzhou (CN); Xiaoming Qian, Suzhou (CN); Qunhua Li, Suzhou (CN); Ming Ji, Suzhou (CN)

(73) Assignee: MAQUET (SUZHOU) CO., LTD., Suzhou (CN)

( * ) Notice: Subject to any disclaimer, the term of this patent is extended or adjusted under 35 U.S.C. 154(b) by 419 days.

(21) Appl. No.: 14/353,739

(22) PCT Filed: Jul. 26, 2013

(86) PCT No.: PCT/CN2013/080161
§ 371 (c)(1),
(2) Date: Apr. 23, 2014

(87) PCT Pub. No.: WO2014/071751
PCT Pub. Date: May 15, 2014

(65) Prior Publication Data
US 2015/0300563 A1  Oct. 22, 2015

(30) Foreign Application Priority Data

Nov. 7, 2012  (CN) .......................... 2012 1 0438413
Nov. 7, 2012  (CN) .......................... 2012 1 0438514
Nov. 7, 2012  (CN) ..................... 2012 2 0580148 U

(51) Int. Cl.
*F16M 13/02*  (2006.01)
*B65B 5/06*  (2006.01)
(Continued)

(52) U.S. Cl.
CPC ........... *F16M 13/027* (2013.01); *A61B 90/50* (2016.02); *B65B 5/06* (2013.01); *B65B 7/2842* (2013.01);
(Continued)

(58) Field of Classification Search
CPC .... A61B 2090/508; A61B 90/50; A61B 90/35
See application file for complete search history.

(56) References Cited

U.S. PATENT DOCUMENTS 5,618,090 A * 4/1997 Montague ............ A61G 12/002
                                                    211/26
6,095,468 A * 8/2000 Chirico .................. F16M 11/04
                                                    248/125.7
(Continued)

FOREIGN PATENT DOCUMENTS

CN       202038502 U    11/2011
CN       202211748 U     5/2012
(Continued)

OTHER PUBLICATIONS

International Search Report dated Oct. 31, 2013 which issued for corresponding application No. PCT/CN2013/080161, 4 pages.

*Primary Examiner* — Bradley Duckworth

(57) ABSTRACT

The present invention relates to a medical ceiling pendant, an apparatus and a method for overall packaging the medical ceiling pendant, wherein the rotary structure of the medical ceiling pendant is hinged to a gas and electric supply box, a second H-shaped bracket and a U-shaped bracket are plugged onto a pallet, and a third H-shaped bracket is mounted onto the U-shaped bracket; one end of the gas and electric supply box is abutted to the pallet, the other end of the gas and electric supply box is lapped onto the second H-shaped bracket, and one end of the rotary structure is lapped onto the third H-shaped bracket; the first H-shaped bracket is plugged onto the pallet, and the other end of the (Continued)

rotary structure is lapped onto the first H-shaped bracket; a protective peripheral board is provided on the pallet from top to bottom, then the outside of the protective peripheral board is provided with a reinforcing peripheral board, finally a cover board is connected to the upper end of the reinforcing peripheral board. The present invention allows overall packaging the medical ceiling pendant formed by connecting the rotary structure and the gas and electric supply box together, thus achieving one box packaging one medical ceiling pendant, greatly decreasing the package cost, easy to transport, lowering the logistical cost, and at the same time improving the field installation efficiency and quality.

8 Claims, 12 Drawing Sheets

(51) Int. Cl.

| | | |
|---|---|---|
| *B65B 7/28* | (2006.01) | |
| *B65B 55/00* | (2006.01) | |
| *B65D 19/18* | (2006.01) | |
| *B65D 19/06* | (2006.01) | |
| *B65D 19/44* | (2006.01) | |
| *F16M 11/20* | (2006.01) | |
| *F16M 11/38* | (2006.01) | |
| *A61B 90/50* | (2016.01) | |

(52) U.S. Cl.
CPC .............. *B65B 55/00* (2013.01); *B65D 19/06* (2013.01); *B65D 19/18* (2013.01); *B65D 19/44* (2013.01); *F16M 11/2014* (2013.01); *F16M 11/38* (2013.01); *F16M 13/022* (2013.01); *B65D 2519/00159* (2013.01); *B65D 2519/00194* (2013.01); *B65D 2519/00338* (2013.01); *B65D 2519/00497* (2013.01); *B65D 2519/00611* (2013.01); *B65D 2519/00621* (2013.01); *B65D 2519/00641* (2013.01); *B65D 2519/00711* (2013.01); *B65D 2519/00815* (2013.01); *B65D 2585/6897* (2013.01)

(56) References Cited

U.S. PATENT DOCUMENTS

| | | | | |
|---|---|---|---|---|
| 6,196,649 | B1* | 3/2001 | Block ................. | A61G 13/107 312/205 |
| 6,364,268 | B1* | 4/2002 | Metelski ............... | F16M 11/04 248/278.1 |
| 6,639,789 | B2* | 10/2003 | Beger .................... | A61B 90/50 248/276.1 |
| 6,659,415 | B2* | 12/2003 | Kummerfeld .......... | F16M 11/04 248/327 |
| 6,817,585 | B2* | 11/2004 | Wagner ................. | F16M 11/04 248/324 |
| 7,065,811 | B2* | 6/2006 | Newkirk ............. | A61M 5/1415 5/600 |
| 7,073,765 | B2* | 7/2006 | Newkirk ................ | A61B 50/10 248/283.1 |
| 7,331,550 | B2* | 2/2008 | Gillespie ............... | F16M 11/08 248/278.1 |
| 7,770,247 | B2* | 8/2010 | Lubbers ................ | F16D 63/008 188/171 |
| 7,770,860 | B1* | 8/2010 | Culpepper ........... | A61G 12/002 248/324 |
| 7,837,674 | B2* | 11/2010 | Cooper ................ | B25J 19/0016 248/280.11 |
| 2003/0076015 | A1* | 4/2003 | Ehrenreich ............ | A61B 50/13 312/209 |
| 2003/0197100 | A1* | 10/2003 | Marchese .............. | A61B 90/50 248/129 |
| 2014/0339377 | A1* | 11/2014 | Tao .......................... | F16L 3/01 248/68.1 |
| 2015/0013783 | A1* | 1/2015 | Palmerton .......... | B01D 46/0036 137/356 |

FOREIGN PATENT DOCUMENTS

| | | |
|---|---|---|
| CN | 102743229 A | 10/2012 |
| CN | 102887303 A | 1/2013 |
| CN | 102895034 A | 1/2013 |
| CN | 202892093 U | 4/2013 |
| CN | 202897213 U | 4/2013 |

\* cited by examiner

MEDICAL CEILING PENDANT, AND APPARATUS AND METHOD FOR OVERALL PACKING MEDICAL CEILING PENDANT

TECHNICAL FIELD

The present invention relates to a medical ceiling pendant, and an apparatus and a method for overall packaging the medical ceiling pendant.

BACKGROUND ART

Medical ceiling pendant is the essential medical device in the modern operating room in the hospital, which is mainly used for terminal-transferring the medial gas, such as oxygen supply, compressed air, nitrogen, etc., in the operating room and the intensive care unit, the lower part of the medical ceiling pendant is provided with a load platform, which facilitates placing some surgical instruments or equipments and meters. As the huge structure size of the medical ceiling pendant, the arms and the box body are separately packaged during the prior packaging and transportation, such packaging process has the defects as follows: 1. there needs two packing box for one medical ceiling pendant, thus resulting in more consumables and higher logistical cost, 2. the gas tubes and the wires on the box body are required to pass through the ceiling pendant arm at the customer's field, thus resulting in time-consuming and labor-consuming, 3. it requires some skills to pass through the gas tubes and the wires in field, thus unable to guarantee the quality.

CONTENTS OF THE INVENTION

The present invention has overcome the deficiencies in the prior art, and provided a simple-structure medical ceiling pendant, and an apparatus and a method for overall packaging the medical ceiling pendant.

To achieve the above-mentioned objects, the present invention employed the technical solutions as follows: a medical ceiling pendant, comprising a rotary structure and a gas and electric supply box, wherein the rotary structure was hinged to the gas and electric supply box, and the rotary structure and the gas and electric supply box can be overall packaged in a packaging apparatus.

In one preferred embodiment of the present invention, the medical ceiling pendant further comprised that the rotary structure consisted of a first shaft, an upper arm, a second shaft, a lower arm and a third shaft which were connected sequentially; the gas and electric supply box consisted of a box body, and a flange which was mounted onto one end of the box body; and the third shaft was connected to the flange via a hinge.

In a preferred embodiment of the present invention, the medical ceiling pendant further comprised that the hinge comprised a first hinge board and a second hinge board with a pin shaft, wherein one end of the first hinge board was pivotally connected to the pin shaft, the other end of the first hinge board was fixed to the third shaft, and the second hinge board was fixed to the flange.

In one preferred embodiment of the present invention, the medical ceiling pendant further comprised that the first hinge board and the second hinge board were respectively provided with a first mounting hole and a second mounting hole, the shaft surfaces of the third shaft and the flange were respectively provided with a first groove and a second groove, the groove ends of the first groove and the second groove were respectively provided with a first threaded hole and a second threaded hole, the first hinge board was fixed onto the third shaft by screwing the first screw sequentially into the first mounting hole and the first threaded hole, and the second hinge board was fixed onto the flange by screwing the second screw sequentially into the second mounting hole and the second threaded hole.

In one preferred embodiment of the present invention, the medical ceiling pendant further comprised that the first mounting hole and the second mounting hole were trumpet-shaped, i.e., one end being small and the other end being large.

A apparatus for overall packaging a medical ceiling pendant, wherein the packaging apparatus can overall package therein the medical ceiling pendant consisted of the rotary structure and the gas and electric supply box which were hinged together, comprised a pallet, and a first H-shaped bracket, a second H-shaped bracket, and a U-shaped bracket which were sequentially mounted onto the pallet, the upper end of the U-shaped bracket was detachably connected with a third H-shaped bracket, the pallet was provided with a protective peripheral board and a reinforcing peripheral board located outside of the protective peripheral board, and the upper end of the reinforcing peripheral board was connected with a cover board.

In a preferred embodiment of the present invention, the packaging apparatus further comprised that one end of the pallet was provided with a fixed block, a first expandable polyethylene board, and a second expandable polyethylene board, the upper end of the second expandable polyethylene board was lapped onto the fixed block, the lower end of the second expandable polyethylene board was connected to the first expandable polyethylene board, the pallet was provided with two first stop blocks, two second stop blocks, and two third stop blocks, which were opposed in pairs, the two first stop blocks, the two second stop blocks, and the two third stop blocks were respectively provided with a first opening, a second opening and a third opening, and the pallet was provided with convex blocks at the four corners.

In a preferred embodiment of the present invention, the packaging apparatus further comprised that the U-shaped bracket was provided with L-shaped openings at both ends, and the lower ends of the third H-shaped bracket were abutted to the L-shaped openings, and provided with the stop blocks at both sides.

In a preferred embodiment of the present invention, the packaging apparatus further comprised that the reinforcing peripheral board was formed by connecting the first reinforcing board and the second reinforcing board; the first reinforcing board comprised a first side board, and a first cuff and a second cuff which were perpendicularly provided at both ends of the first side board, and the second reinforcing board comprised a second side board, and a third cuff and a fourth cuff which were perpendicularly provided at both ends of the second side board.

A method for overall packaging a medical ceiling pendant, using the above-mentioned packaging apparatus, comprising the following steps:

(1) the second H-shaped bracket and the U-shaped bracket were plugged onto the pallet, and the third H-shaped bracket was mounted onto the U-shaped bracket;

(2) one end of the gas and electric supply box was abutted to the pallet, the other end of the gas and electric supply box was lapped onto the second H-shaped bracket, and one end of the rotary structure was lapped onto the third H-shaped bracket;

(3) the first H-shaped bracket was plugged onto the pallet, and one end of the rotary structure was lapped onto the first H-shaped bracket;

(4) the protective peripheral board was provided onto the pallet from top to bottom, then the outside of the protective peripheral board was provided with the reinforcing peripheral board, finally the cover board was connected to the upper end of the reinforcing peripheral board.

The present invention has solved the deficiencies present in the background art, the present invention has a simple structure, and is convenient and easy to use, can overall package the medical ceiling pendant formed by connecting the rotary structure and the gas and electric supply box together, so that it is achieved that one medical ceiling pendant is packaged in one packing box, thus the packaging cost is greatly decreased; and as there are some suitable supporting points for the overall packaged medical ceiling pendant, thus it facilitates assembling in the workshop, and at the same time during the transportation, the medical ceiling pendant can be protected, and the transportation is convenient and easy, the logistical cost is low, it is unnecessary for the customer to pass through the gas tubes and the wires in field, during the installation in the customer's field, the medical ceiling pendant can be better protected and the installation process is more fluent, thus the field installation efficiency and quality are improved.

DESCRIPTION OF THE ACCOMPANYING DRAWINGS

Hereinbelow, the present invention was further illustrated in combination with the accompanying drawings and the embodiments.

wherein: 1. rotary structure, 2. gas and electric supply box, 3. packaging apparatus, 4. first shaft, 5. upper arm, 6. second shaft, 7. lower arm, 8. third shaft, 9. box body, 10. flange, 11. hinge, 12. first hinge board, 13. pin shaft, 14. second hinge board, 15. first mounting hole, 16. second mounting hole, 17. first groove, 18. second groove, 19. first threaded hole, 20. second threaded hole, 21. first screw, 22. second screw, 23. pallet, 24. first H-shaped bracket, 25. second H-shaped bracket, 26. U-shaped bracket, 27. third H-shaped bracket, 28. protective peripheral board, 29. reinforcing peripheral board, 30. cover board, 31. fixed block, 32. first expandable polyethylene board, 33. second expandable polyethylene board, 34. first stop block, 35. second stop block, 36. third stop block, 37. first opening, 38. second opening, 39. third opening, 40. convex block, 41. L-shaped opening, 42. stop block, 43. first reinforcing board, 44. second reinforcing board, 45. first side board, 46. first cuff, 47. second cuff, 48. second side board, 49. third cuff, 50. fourth cuff, 51. first mounting hole, 52. second mounting hole, 53. third mounting hole, 54. fourth mounting hole.

EMBODIMENTS

Now, the present invention is further illustrated in detail in combination with the accompanying drawings and the embodiments, wherein the accompanying drawings are all simplified schematic diagrams, which are used to schematically illustrate the basic structure of the present invention, thus they only show the constitution related to the present invention.

Figure 1:
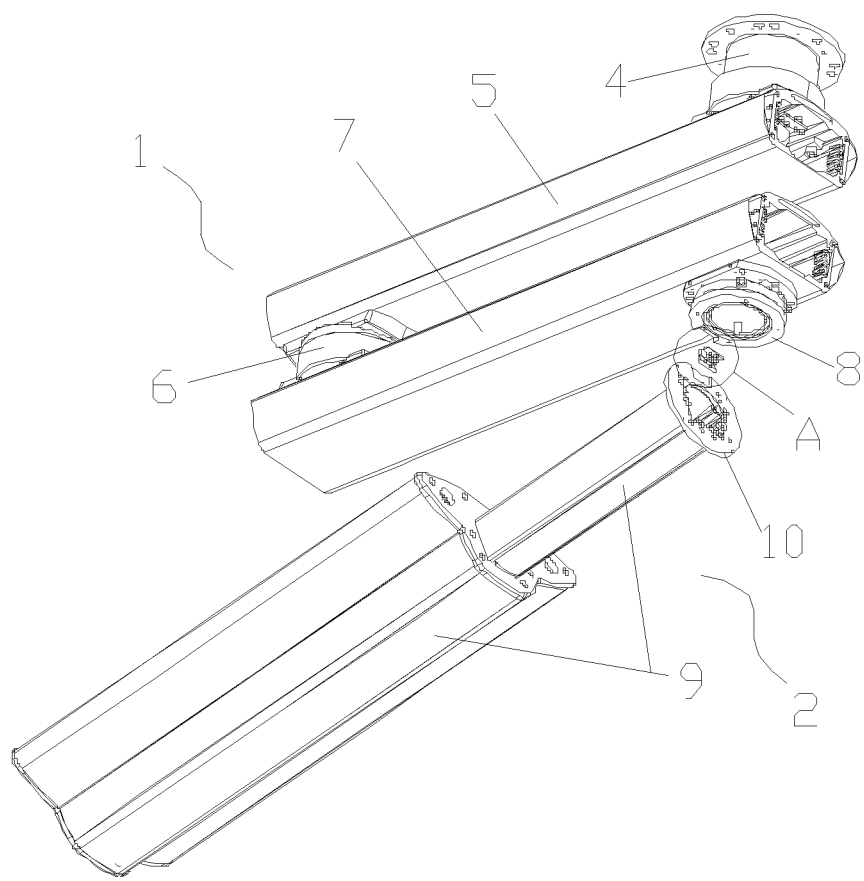
FIG. 1 is a schematic diagram for assembling the medical ceiling pendant according to a preferred embodiment of the present invention.
Figure 2:
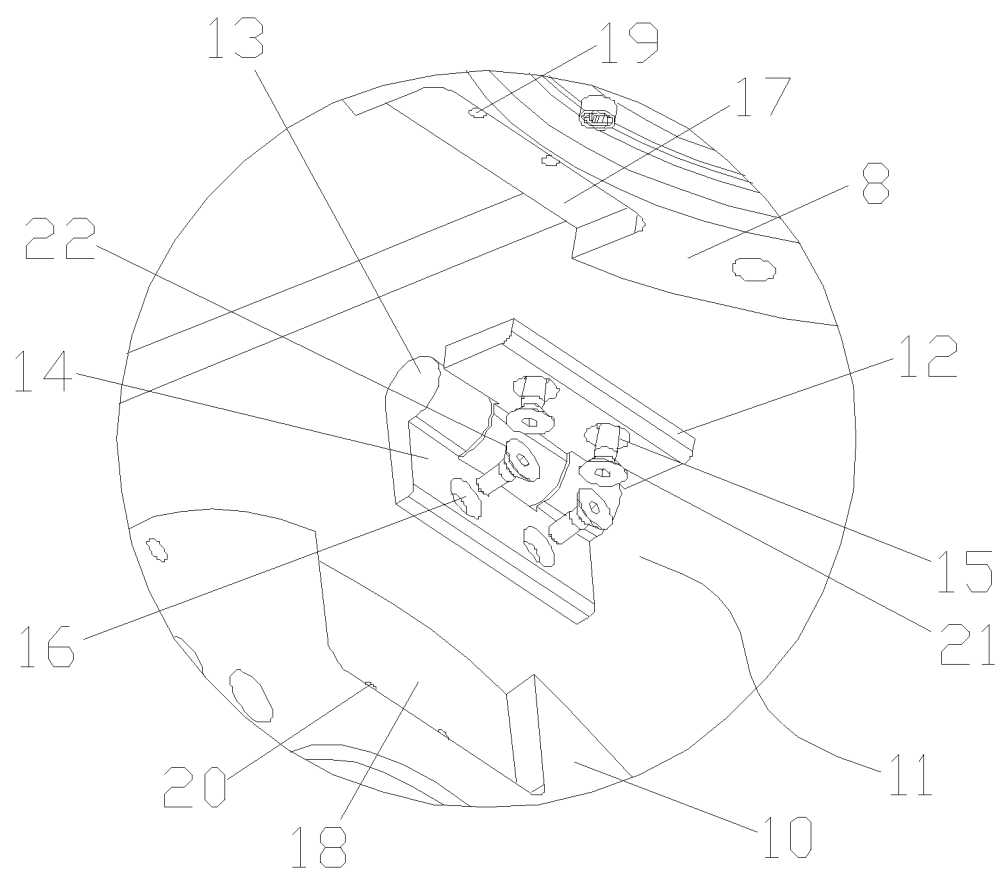
FIG. 2 is an enlarged schematic diagram of A in FIG. 1.
Figure 3:
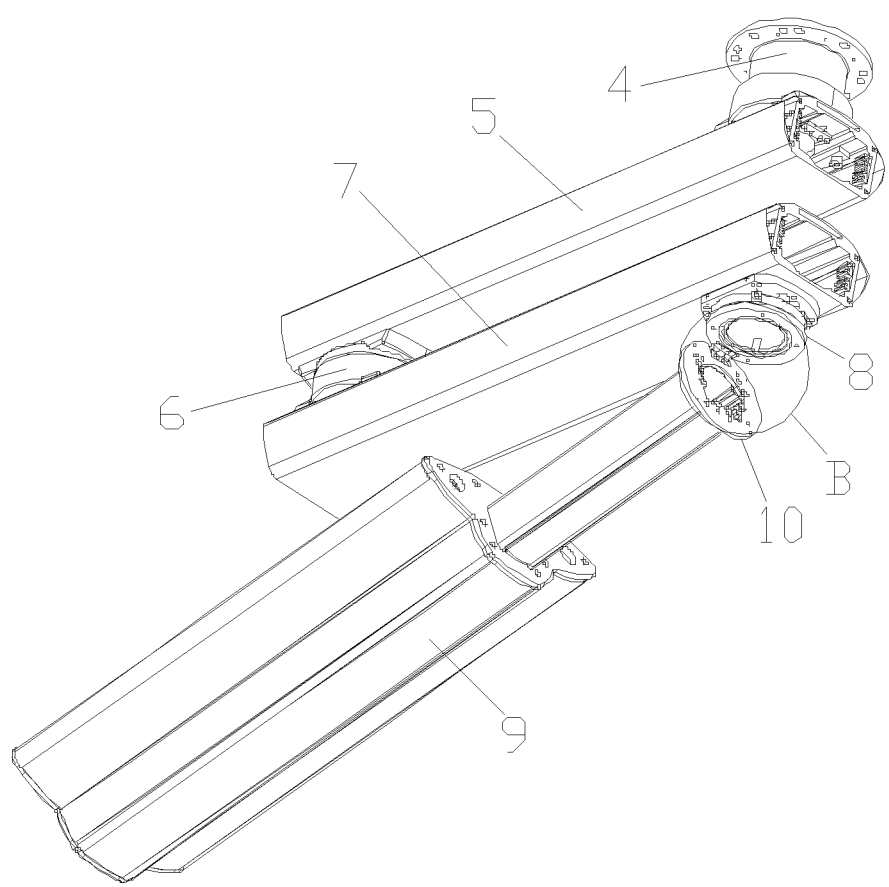
FIG. 3 is a structural schematic diagram of the medical ceiling pendant according to a preferred embodiment of the present invention.
Figure 4:
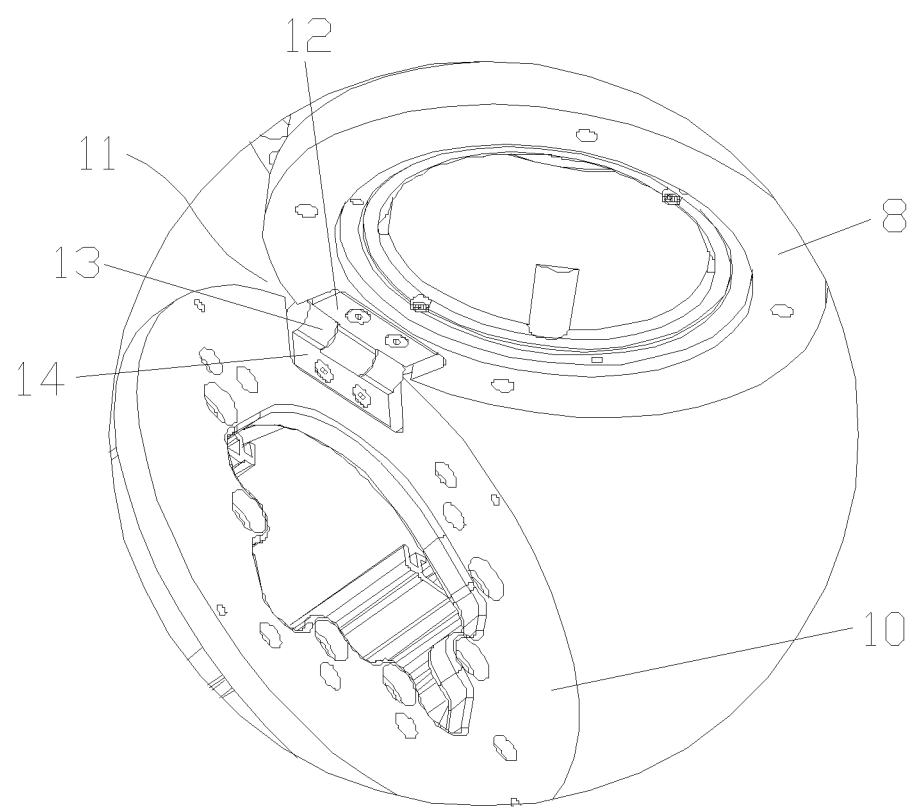
FIG. 4 is an enlarged schematic diagram of B in FIG. 3.
Figure 7:
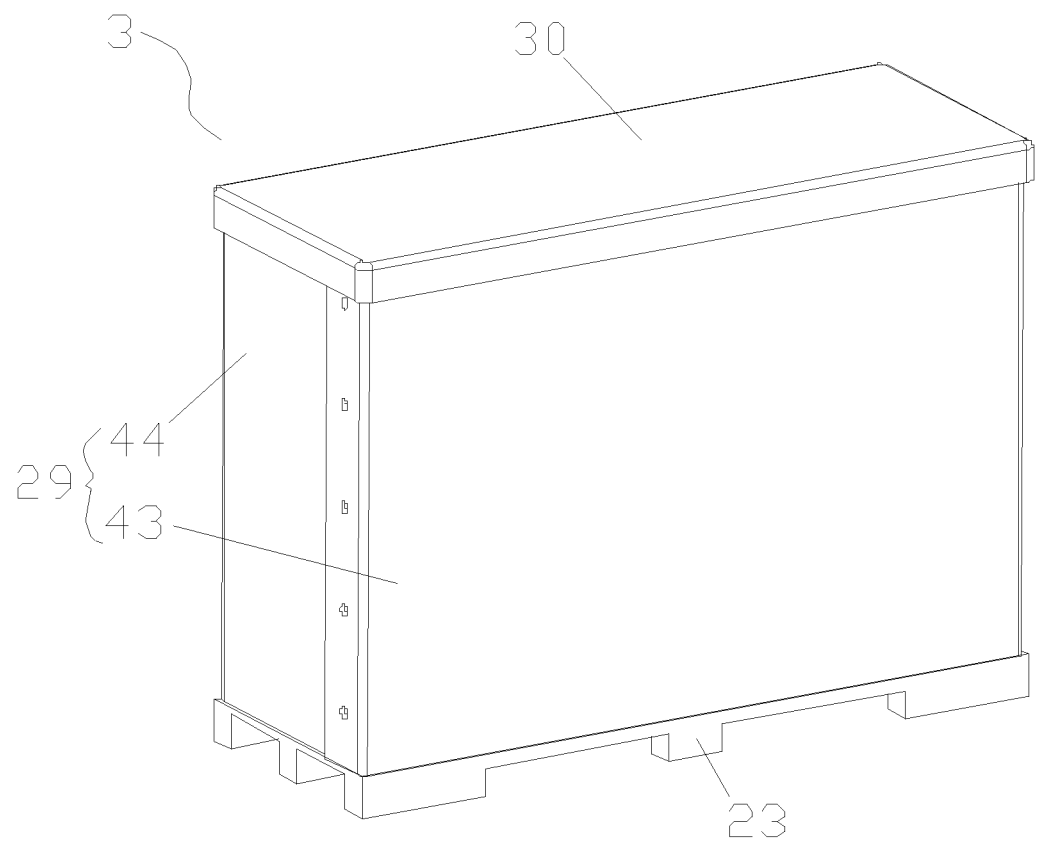
FIG. 7 is a schematic diagram of the final product of the packaging apparatus according to a preferred embodiment of the present invention.
Figure 9:
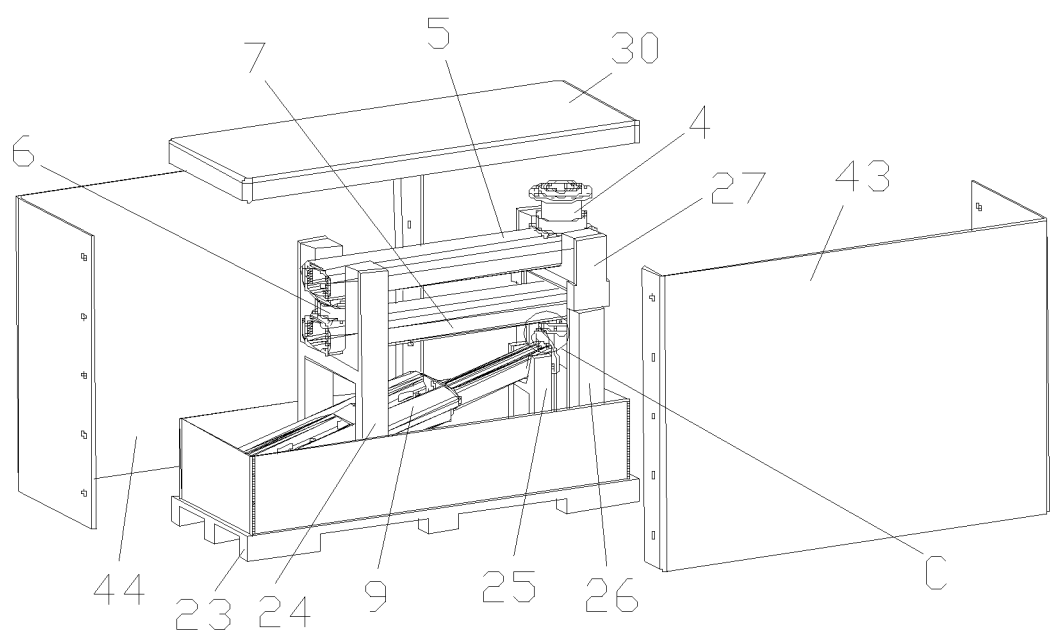
FIG. 9 is a schematic diagram for packaging the medical ceiling pendant according to a preferred embodiment of the present invention.

As shown in FIGS. 1-4, 7 and 9, a medical ceiling pendant, comprising a rotary structure 1 and a gas and electric supply box 2, wherein the rotary structure 1 was hinged to the gas and electric supply box 2, and the rotary structure 1 and the gas and electric supply box 2 can be overall packaged in a packaging apparatus 3.

The rotary structure 1 consisted of a first shaft 4, an upper arm 5, a second shaft 6, a lower arm 7, and a third shaft 8, which were sequentially connected, the gas and electric supply box 2 consists of a box body 9 and a flange 10 which was mounted to one end of the box body 9, and the third shaft 8 was connected to the flange 10 via a hinge 11.

The hinge 11 comprised a first hinge board 12 and a second hinge board 14 with a pin shaft 13, one end of the first hinge board 12 was pivotally connected to the pin shaft 13, the other end of the first hinge board 12 was fixed to the third shaft 8, and the second hinge board 14 was fixed onto the flange 10.

It is preferred in the present invention that the first hinge board 12 and the second hinge board 14 were respectively provided with a first mounting hole 15 and a second mounting hole 16, and the shaft surfaces of the third shaft 8 and the flange 10 were respectively provided with a first groove 17 and a second groove 18, the depths of the first groove 17 and the second groove 18 were respectively higher than the thicknesses of the first hinge board 12 and the second hinge board 14, thus facilitating the first hinge board 12 and the second hinge board 14 being overall placed in the first groove 17 and the second groove 18, the groove bottoms of the first groove 17 and the second groove 18 were respectively provided with a first threaded hole 19 and a second threaded hole 20, the first hinge board 12 was fixed onto the third shaft 8 by screwing the first screw 21 subsequently into the first mounting hole 15 and the first threaded hole 19, the second hinge board 14 was fixed onto the flange 10 by screwing the second screw 22 sequentially into the second mounting hole 16 and the second threaded hole 20, both the first mounting hole 15 and the second mounting hole 16 were trumpet-shaped, ie., one end being small and the other end being large, so that the head of the first screw 21 and the head of the second screw 22 were respectively located in the first mounting hole 15 and the second mounting hole 16, without being exposed to outside, thus avoiding the interference caused when fitting to the third shaft 8 and the flange 10.

Figure 5:
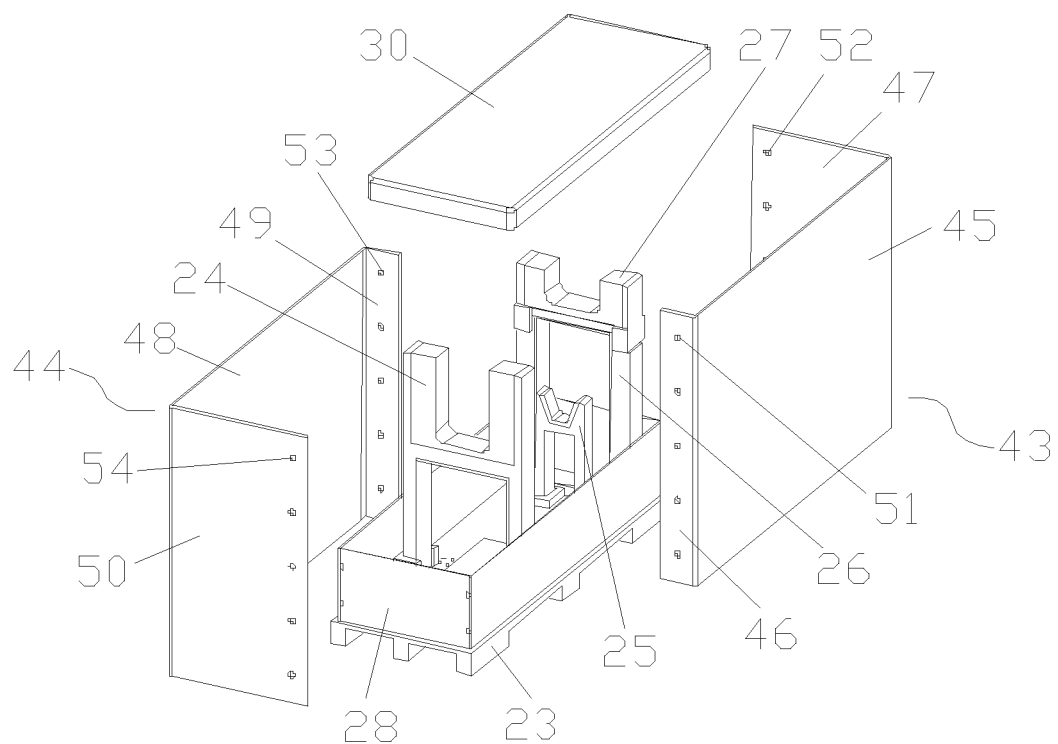
FIG. 5 is a schematic diagram for assembling the packaging apparatus according to a preferred embodiment of the present invention.
Figure 6:
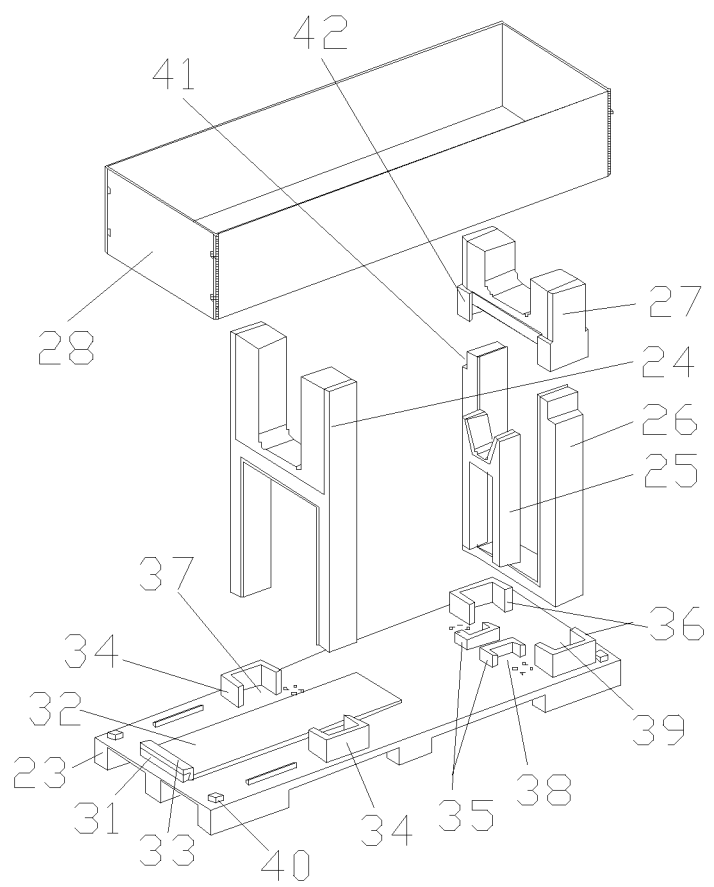
FIG. 6 is an exploded structural schematic diagram of the packaging apparatus, without the reinforcing peripheral board and the cover board, according to a preferred embodiment of the present invention.
Figure 8:
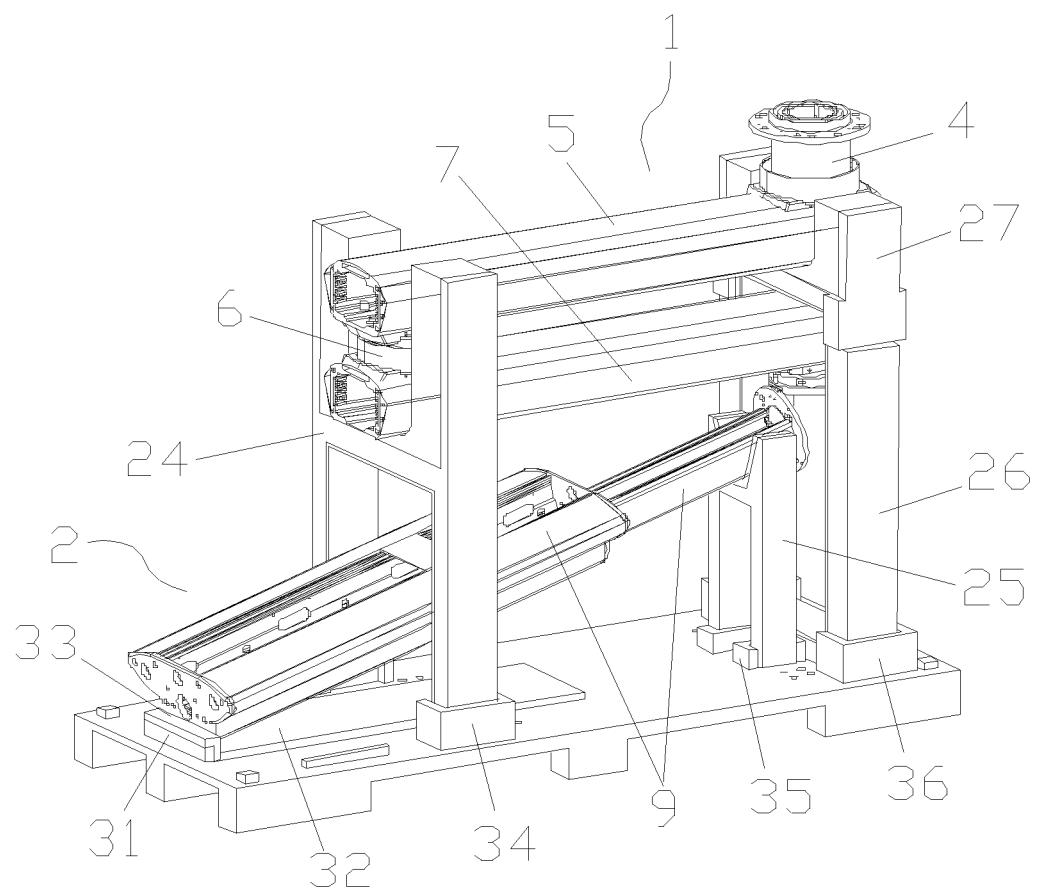
FIG. 8 is a schematic diagram for supporting the medical ceiling pendant according to a preferred embodiment of the present invention.
Figure 10:
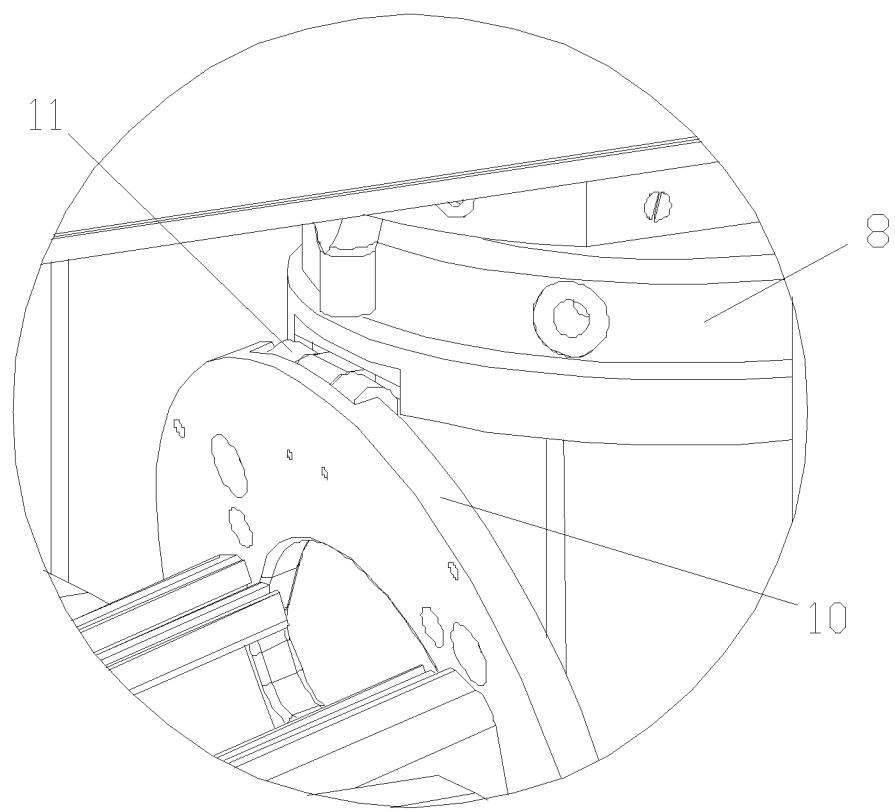
FIG. 10 is an enlarged schematic diagram of C in FIG. 9.

As shown in FIGS. 5-10, an overall packaging apparatus for a medical ceiling pendant, where the packaging apparatus 3 can overall package therein the medical ceiling pendant consisted of the rotary structure 1 and the gas and electric supply box 2, which were hinged together, comprised a pallet 23, and a first H-shaped bracket 24, a second H-shaped bracket 25 and a U-shaped bracket 26 which were sequentially mounted onto the pallet 23, the upper end of the U-shaped bracket 26 was detachably connected with a third H-shaped bracket 27, the pallet 23 was provided with a protective peripheral board 28 and a reinforcing peripheral board 29 located outside of the protective peripheral board 28, the upper end of the reinforcing peripheral board 29 was connected with a cover board 30, and the reinforcing peripheral board 29 and the cover board 30 were made of a high-strength paper.

In order to avoid the abrasion of the gas and electric supply box 2 of the medical ceiling pendant during the transportation and the installation processes, one end of the pallet 23 was provided with a fixed block 31, a first expandable polyethylene board 32 and a second expandable polyethylene board 33, the upper end of the second expandable polyethylene board 33 was lapped onto the fixed block 31, and the lower end of the second expandable polyethylene board 33 was connected to the first expandable polyethylene board 32, in order to facilitate the first H-shaped bracket 24, the second H-shaped bracket 25 and the U-shaped bracket 26 being plugged onto the pallet 23, the pallet 23 was provided with two first stop blocks 34, two second stop blocks 35, and two stop blocks 36, which were opposed in pairs, the two first stop blocks 34, the two second stop blocks 35 and the two third stop blocks 36 were respectively provided with a first opening 37, a second opening 38, and a third opening 39, the pallet 23 is provided with the convex blocks 40 at the four corners, facilitating the protective peripheral board 28 being located on the pallet 23.

The U-shaped bracket 26 was provided with L-shaped openings 41 at both ends, and the lower ends of the third H-shaped bracket 27 were abutted to the L-shaped openings 41, and provided with the stop blocks 42 at both sides, the stop block 42 can prevent the third H-shaped bracket 27 from sliding in the left and right direction.

The reinforcing peripheral board 29 was formed by connecting the first reinforcing board 43 and the second reinforcing board 44, the first reinforcing board 43 comprised a first side board 45, and a first cuff 46 and a second cuff 47 which were perpendicularity provided at both ends of the first side board 45, the second reinforcing board 44 comprised a second side board 48, and a third cuff 49 and a fourth cuff 50 which were provided at both ends of the second side board 48, in order to facilitate the fixed connection between the first reinforcing board 43 and the second reinforcing board 44, the free ends of the first cuff 46, the second cuff 47, the third cuff 49, and the fourth cuff 50 were respectively provided with a plurality of the first mounting holes 51, the second mounting holes 52, the third mounting holes 53 and the fourth mounting holes 54, in the perpendicular direction, it was preferred in the present invention that the numbers of the first mounting holes 51, the second mounting holes 52, the third mounting holes 53, and the fourth mounting holes were each 5.

Figure 11:
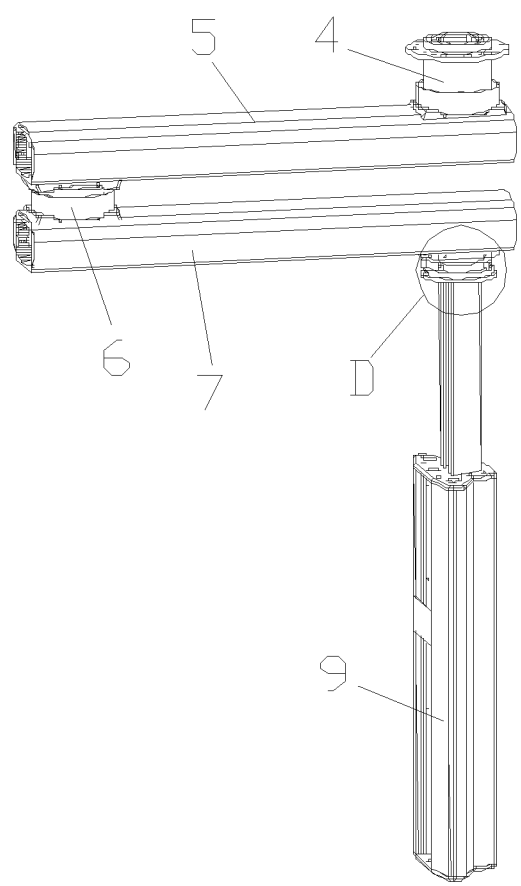
FIG. 11 is a structural schematic diagram of the medical ceiling pendant, after the field installation is completed, according to a preferred embodiment according to the present invention.
Figure 12:
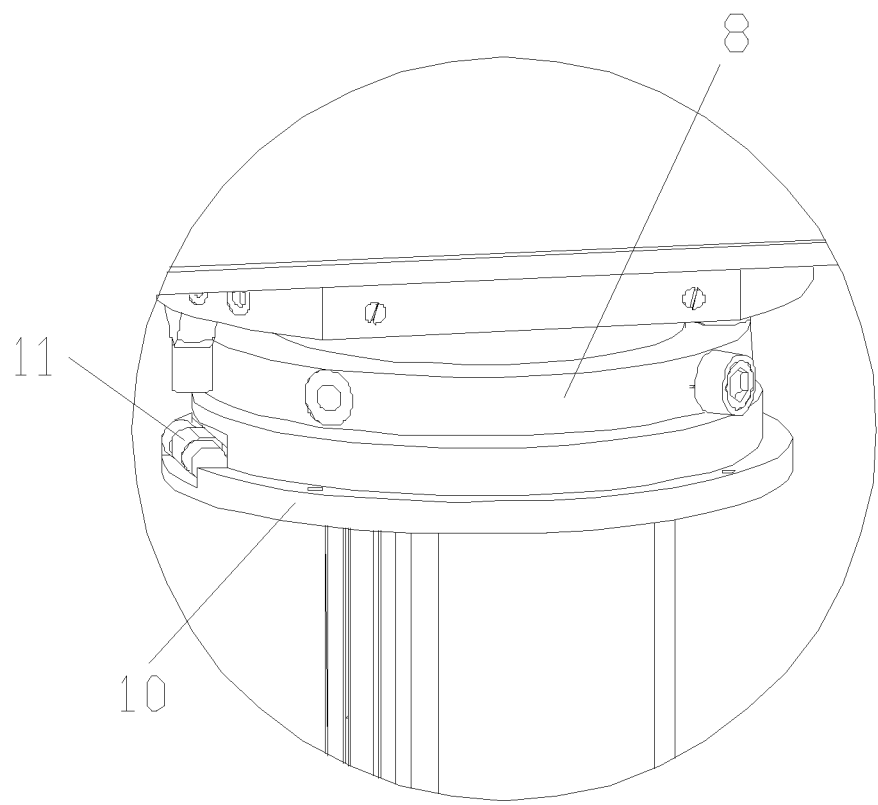
FIG. 12 is an enlarged schematic diagram of D in FIG. 11.

As shown in FIGS. 1-12, a method for overall packaging a medical ceiling pendant, using a packaging apparatus 3, comprising the following steps:

(1) a rotary structure 1 was formed by assembling together a first shaft 4, an upper arm 5, a second shaft 6, a lower arm 7 and a third shaft 8 sequentially, wherein the first shaft 4 was located at the uppermost, and at the same time, the flange 10 was assembled at the front end of the box body 9 to form a gas and electric supply box 2;

(2) the ends of the second H-shaped bracket 25 and the U-shaped bracket 26 were respectively plugged into the two second openings 38 and the two third openings 39 of the two second stop blocks 35 and the two third stop blocks 36 on the pallet 23, the lower ends of the third H-shaped bracket 27 were plugged into the L-shaped openings 41 of the U-shaped bracket 26, and at the same time being limited by the two stop blocks 42 in the left and right direction.

(3) the pallet 23 was provided with a fixed block 31, a first expandable polyethylene board 32 and a second expandable polyethylene board 33;

(4) one end of the box body 9 was abutted to the first expandable polyethylene board 32 and the second expandable polyethylene board 33, which were located on the pallet 23, the other end of the box body 9 was lapped onto the second H-shaped bracket 25, one end of the upper arm 5 was lapped onto the third H-shaped bracket 27, and one end of the lower arm 7 was located below the third H-shaped bracket 27;

(5) the lower ends of the first H-shaped bracket 24 were plugged into the two first openings 37 of the two first stop blocks 34 on the pallet 23, and the other end of the lower arm 7 was lapped onto the first H-shaped bracket 24;

(6) the first hinge board 12 of the hinge 11 was fixed into the first groove 17 of the third shaft 8 by screwing the first screw 21 sequentially into the first mounting hole 15 and the first threaded hole 19, and the second hinge board 14 of the hinge 11 was fixed into the second groove 18 of the flange 10 by screwing the second screw 22 sequentially into the second mounting hole 16 and the second threaded hole 20, so that one end of the third shaft 8 was hinged together with one end of the flange 10;

(7) the gas tubes and the wires were sequentially passed through the third shaft 8, the lower arm 7, the second shaft 6, the upper arm 5 and the first shaft 4;

(8) the protective peripheral board 28 was sleevedly provided on the pallet 23 from top to bottom, then the outside of the protective peripheral board 28 was provided with a reinforcing peripheral board 29, the reinforcing peripheral board 29 was respectively clicked into the first mounting hole 51, the fourth mounting hole 54 and the third mounting hole 53, the second mounting hole 52 via snaps (no shown in the figures), so that the first reinforcing board 43 and the second reinforcing board 44 were fixed together, finally the cover board 30 was sleeved on the upper end of the reinforcing peripheral board 29.

Of course, the fixation between the protective peripheral board 28 and the reinforcing peripheral board 29 was not limited to such mode, the reinforcing peripheral board 29 can also make the first reinforcing board 43 and the second reinforcing board 44 fixed together by screwing the screws respectively into the first mounting hole 51, the fourth mounting hole 54 and the third mounting hole 53, the second mounting hole 52.

A method for overall packaging a medical ceiling pendant, using a packaging apparatus 3 (also can employ anther embodiment), comprising the following steps:

(1) a rotary structure 1 was formed by assembling together a first shaft 4, an upper arm 5, a second shaft 6, a lower arm 7 and a third shaft 8 sequentially, wherein the first shaft 4 was located at the uppermost, and at the same time the flange 10 was assembled at the front end of the box body 9 to form a gas and electric supply box 2;

(2) the first hinge board 12 of the hinge 11 was fixed into the first groove 17 of the third shaft 8 by screwing the first screw 21 sequentially into a first mounting hole 15 and a first threaded hole 19, and the second hinge board 14 of the hinge 11 was fixed into the second groove 18 of the flange 10 by screwing the second screw 22 sequentially into a second mounting hole 16 and a second threaded holes 20, so that one end of the third shaft 8 was hinged together with one end of the flange 10;

(3) the gas tubes and the wires were sequentially passed through the third shaft 8, the lower arm 7, the second shaft 6, the upper arm 5 and the first shaft 4;

(4) the lower ends of the second H-shaped bracket 25 and the U-shaped bracket 26 were respectively plugged into the two second openings 38 and the two third openings 39 of the two second stop blocks 35 and the two third stop blocks 36 on the pallet 23, the lower ends of the third H-shaped bracket 27 were inserted into the L-shaped openings 41 of the U-shaped bracket 26, and at the same time being limited by the two stop blocks 42 in the left and right direction;

(5) the pallet 23 was provided with a stop block 31, a first expandable polyethylene board 32, and a second expandable polyethylene board 33;

(6) one end of the box body 9 was abutted to the first expandable polyethylene board 32 and the second expandable polyethylene board 33, which were located on the pallet 23, the other end of the box body 9 was lapped onto the second H-shaped bracket 25, one end of the upper arm 5 was lapped onto the third H-shaped bracket 27, and one end of the lower arm 7 was located below the third H-shaped bracket 27;

(7) the lower ends of the first H-shaped bracket 24 were plugged into the two first openings 37 of the two stop blocks 34 on the pallet 23, and the other end of the lower arm 7 was lapped onto the first H-shaped bracket 24;

(8) the protective peripheral board 28 was sleevedly provided on the pallet 23 from top to bottom, then the outside of the protective peripheral board 28 was provided with a reinforcing peripheral board 29, the reinforcing peripheral board 29 was respectively clicked into the first mounting hole 51, the fourth mounting hole 54 and the third mounting hole 53, the second mounting hole 52 via snaps (not shown in the figures), so that first reinforcing board 43 and the second reinforcing board 44 were fixed together, finally the cover board 30 was sleeved on the upper end of the reinforcing peripheral board 29.

Of course, the fixation of between the protective peripheral board 28 and the reinforcing peripheral board 29 was not limited to such mode, the reinforcing peripheral board 29 can also make the first reinforcing board 43 and the second reinforcing board 44 fixed together by screwing the screws sequentially into the first mounting hole 51, the fourth mounting hole 54 and the third mounting hole 53, the second mounting hole 52.

When the customer carried out the field installation, first the cover board 30 and the reinforcing peripheral board 29 were removed off, then the pallet 23 was lift up by employing a forklift truck, the first shaft 4 was mounted on the anchor of the ceiling, when the forklift truck slowly declined, the box body 9 slowly dropped down around the hinge 11 as the pallet 23 declining until the box body 9 detaching from the pallet 23, then the third H-shaped bracket 27 was removed off, finally the box body 9 was straightened, so that the flange 10 was fitted with the third shaft 8, and the flange 10 was fixed to the third shaft 8 by employing screws (not shown in the figures), without taking off the hinge 11 during the overall process.

Hereinbefore, under the illumination of the ideal embodiments of the present invention, various modifications and changes can completely be made by those skilled in the art through the above-mentioned description, without departing from the technical idea range of the present invention. The technical range of the present invention is not limited to the contents of the description, which should be identified according to the range of the claims.

The invention claimed is:
1. A medical ceiling pendant, comprising:
a rotary structure; and
a gas and electric supply box;
wherein the rotary structure is hinged to the gas and electric supply box;
wherein the rotary structure and the gas and electric supply box are configured to be overall packaged in a packaging apparatus;
wherein the gas and electric supply box includes a box body and a flange that is mounted at one end of the box body;
wherein the rotary structure is connected to the flange via a hinge;
wherein the hinge includes a first hinge board and a second hinge board having a pin shaft;
wherein a first end of the first hinge board is pivotally connected to the pin shaft, a second end of the first hinge board is fixed to the rotary structure, and the second hinge board is fixed to the flange;
wherein a surface of the rotary structure includes a first groove and a surface of the flange includes a second groove; and
wherein a depth of the first groove is larger than a thickness of the first hinge board.
2. The medical ceiling pendant of claim 1, wherein
the rotary structure includes a first shaft, an upper arm, a second shaft, a lower arm, and a third shaft, which are connected sequentially.
3. The medical ceiling pendant of claim 2, wherein the first hinge board and the second hinge board are respectively provided with a first mounting hole and a second mounting hole, the groove bottoms of the first groove and the second groove are respectively provided with a first threaded hole and a second threaded hole, the first hinge board is fixed onto the third shaft by screwing a first screw sequentially into the first mounting hole and the first threaded hole, and the second hinge board is fixed onto the flange by screwing a second screw sequentially into the second mounting hole and the second threaded hole.
4. The medical ceiling pendant of claim 3, wherein both the first mounting hole and the second mounting hole are trumpet-shaped, with a first end being smaller than a second end.
5. The medical ceiling pendant of claim 1, wherein a depth of the second groove is larger than a thickness of the second hinge board.
6. A medical ceiling pendant, comprising:
a rotary structure; and
a gas and electric supply box;
wherein the rotary structure is hinged to the gas and electric supply box;

wherein the rotary structure and the gas and electric supply box are configured to be overall packaged in a packaging apparatus;

wherein the gas and electric supply box includes a box body and a flange that is mounted at one end of the box body;

wherein the rotary structure is connected to the flange via a hinge;

wherein the hinge includes a first hinge board and a second hinge board having a pin shaft;

wherein a first end of the first hinge board is pivotally connected to the pin shaft, a second end of the first hinge board is fixed to the rotary structure, and the second hinge board is fixed to the flange;

wherein a surface of the rotary structure includes a first groove and a surface of the flange includes a second groove;

wherein a depth of the first groove is larger than a thickness of the first hinge board; and wherein a depth of the second groove is larger than a thickness of the second hinge board.

7. The medical ceiling pendant of claim 6, wherein the rotary structure includes a first shaft, an upper arm, a second shaft, a lower arm, and a third shaft, which are connected sequentially.

8. A medical ceiling pendant, comprising:
a rotary structure; and
a gas and electric supply box;
wherein the rotary structure is hinged to the gas and electric supply box;

wherein the rotary structure and the gas and electric supply box are configured to be overall packaged in a packaging apparatus;

wherein the gas and electric supply box includes a box body and a flange that is mounted at one end of the box body;

wherein the rotary structure is connected to the flange via a hinge;

wherein the hinge includes a first hinge board and a second hinge board having a pin shaft;

wherein a first end of the first hinge board is pivotally connected to the pin shaft, a second end of the first hinge board is fixed to the rotary structure, and the second hinge board is fixed to the flange;

wherein a surface of the rotary structure includes a first groove and a surface of the flange includes a second groove;

wherein a depth of the first groove is larger than a thickness of the first hinge board;

wherein the first hinge board includes a first mounting hole; and wherein the first mounting hole includes a first end and a second end, the first end being smaller than the second end.

* * * * *